United States Patent [19]

Lawton

[11] 4,016,866
[45] Apr. 12, 1977

[54] IMPLANTABLE ELECTROCHEMICAL SENSOR

[75] Inventor: Richard W. Lawton, Schenectady, N.Y.

[73] Assignee: General Electric Company, Schenectady, N.Y.

[22] Filed: Dec. 18, 1975

[21] Appl. No.: 641,833

[52] U.S. Cl. ............... 128/2 E; 128/2.1 E; 204/195 B

[51] Int. Cl.² .................................. A61B 5/00

[58] Field of Search ............ 128/2 E, 2.1 E; 204/195 R, 195 B, 195 F, 1 H

[56] References Cited

UNITED STATES PATENTS

| | | | |
|---|---|---|---|
| 2,168,867 | 8/1939 | George | 204/195 F X |
| 3,151,052 | 9/1964 | Arthur et al. | 204/195 F |
| 3,249,103 | 5/1966 | Woodhouse | 128/2.1 E |
| 3,869,354 | 3/1975 | Montalvo, Jr. | 204/195 B X |
| 3,878,830 | 4/1975 | Bicher | 128/2 E |

OTHER PUBLICATIONS

Joseph, "Heterogeneous . . . Protein Solutions," J. of Biol. Chemistry, vol. 126, pp. 389–405, 1938.

*Primary Examiner*—Robert W. Michell
*Assistant Examiner*—Lee S. Cohen
*Attorney, Agent, or Firm*—Charles T. Watts; Joseph T. Cohen; Jerome C. Squillaro

[57] ABSTRACT

This in vivo sensor assembly, consisting of a sensing electrode and an insertion catheter, is capable of calibration and recalibration in situ without blood sampling because the sensing electrode can be retracted into its insertion catheter where it can be contacted with calibrating solution furnished by a drip line in which the reference electrode also contacts the calibrating solution.

4 Claims, 2 Drawing Figures

IMPLANTABLE ELECTROCHEMICAL SENSOR

The present invention relates generally to the art of measuring or monitoring ion activity in vital fluids, and is more particularly concerned with a novel implantable specific ion sensor assembly having special utility for in vivo monitoring applications.

CROSS REFERENCE

This invention is related to that of U.S. patent application Ser. No. 620,707, filed Oct. 8, 1975, in the names of Oliver H. LeBlanc, Jr., Leonard W. Niedrach and W. H. Stoddard, Jr., and assigned to the assignee hereof, in which the concept of locating the reference electrode outside the catheter and using the infusion isotonic solution as a salt bridge between the blood and the reference electrode is disclosed and claimed.

This invention is also related to that of U.S. patent application Ser. No. 491,772, filed July 24, 1974, now abandoned, and assigned to the assignee hereof in which the concept of providing a salt bridge in the form of a solution of known ion content in which the reference electrode is immersed and within which it equilibrates in an extension of the vessel containing the sensing electrode is disclosed and claimed.

BACKGROUND OF THE INVENTION

Sterile, disposable carbon dioxide and pH sensors of the types disclosed in the above-referenced patent applications are calibrated in vitro prior to use, but because of potential sensor drift, they must be recalibrated periodically during use to verify sensor readings. This is done in accordance with established practice by withdrawing a sample of the patient's blood by means of a syringe connected to the side arm of the catheter containing the sensor and measuring the electrochemical activity of the ion of interest using standard laboratory techniques. Alternatively, a blood sample may be obtained by a separate arterial puncture, or the sensor may be removed for in vitro calibration. There are significant disadvantages to each of these alternatives. They are time-consuming and require special laboratory services and, in addition, one requires multiple blood vessel penetrations while another presents the possibility of loss of sterility, sensor damage or clot formation within the catheter system.

SUMMARY OF THE INVENTION

The necessity for choosing between these alternatives can be avoided and additional new advantages of economy and utility can be obtained through the application of my novel concept to be described. In particular, the electrochemical sensor of this invention does not require withdrawal of blood for calibration purposes and yet can be calibrated and recalibrated in situ. Moreover, such testing can be done quickly, easily and with a high precision without involving laboratory services. Additionally, this invention affords a choice of calibrating solutions and, in fact, in some circumstances the infusion solution normally provided through the drip line of the catheter system can itself serve this calibration function.

My basic concept is to couple the sensing electrode and the reference electrode for calibration purposes and to uncouple them for blood measurement purposes without at any time changing the position of the implanted catheter in a blood vessel. Coupling is provided through the infusion electrolyte or other solution suitable for calibration use, the sensing electrode being movable relative to the catheter so that the electrochemically active portion is within the open or leading end of the catheter, the calibrating fluid surrounding this active portion and forming an electrochemical pathway between the sensor and the reference electrode.

In accordance with this invention, means implementing this new concept are provided for axially moving the sensing electrode relative to the catheter while maintaining seals against leakage of liquid around the sensing electrode into the trailing end of the catheter and preventing entry of blood into the leading end of the catheter and, therefore, blood contact with the electrochemically active area of the sensor during calibration.

DESCRIPTION OF THE DRAWINGS

Those skilled in the art will gain a further and better understanding of this invention on consideration of the detailed description set forth below taken in conjunction with the drawings accompanying and forming a part of this specification, in which.

DETAILED DESCRIPTION OF THE INVENTION

Figure 1:
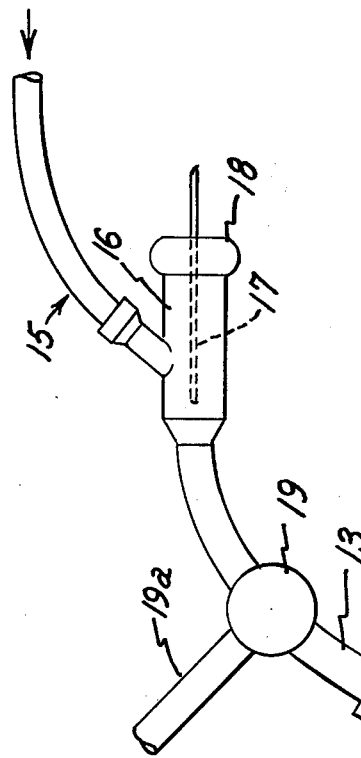
FIG. 1 is an enlarged side elevational view, partly in section, of a sensor assembly embodying this invention in preferred form, the sensing electrode being in the "measurement" position.

As illustrated in the drawings, in vivo specific ion sensor assembly 10 includes a catheter 11 having side arm 12 to receive conduit 13 of a drip line indicated generally at 15 through which isotonic solution electrolyte or suitable specially formulated calibration solution can be introduced into catheter 11. Drip line 15 is like that disclosed in the above-referenced U.S. patent application Ser. No. 620,707, reference electrode 17 in the form of a silver wire bearing a silver chloride coating being disposed in an enlarged section 16 of conduit 13 and extending through cap 18 tightly sealing the reference electrode access opening in conduit section 16. The reference electrode is connected by a shielded cable to a pH meter (both of which are not shown). Alternatively, the reference electrode may embody an intermediate electrolyte bridge such as that disclosed in referenced U.S. patent application Ser. No. 491,772, now abandoned. Flow of electrolyte or calibration solution through conduit 13 is regulated by three-way stopcock 19. The stopcock with its side arm 19a provides an alternate means of injecting the calibrating solution by means of a syringe (not shown).

Open leading end 20 of catheter 11 in use of this assembly is implanted in an artery for discharge of infusion solution 21 continuously or intermittently into the bloodstream at a point slightly downstream from electrochemically active tip 22 of sensing electrode 23 which is of the same construction and mode of operation as that disclosed and claimed in U.S. patent application Ser. No. 491,772. The insulated lead of electrode 23 extends generally axially through catheter 11 and through a guard tube 25 and catheter cap 27 to which the guard is attached as shown at 29, and is connected by a second shielded cable to a pH meter (not shown). The leading end of guard tube 25 is positioned near the side arm 12 discharge opening and is closed to the entrance of liquid into the tube by means of epoxy cement 31 or other suitable potting material which fills tube 25 and also serves to bond the sensing electrode lead to the guard tube. A sealing gland in the form of a short, tapered silicone rubber tube 33 secured at its wide end to the inner wall of catheter 11 above the side arm discharge opening, pressure seals at its narrow end against an annular portion of guard tube 25, preventing liquid flow between the catheter and guard tube. Thus, while permitting axial motion of the guard tube relative to catheter between measurement and calibration positions, this gland maintains a liquid-tight seal.

Figure 2:
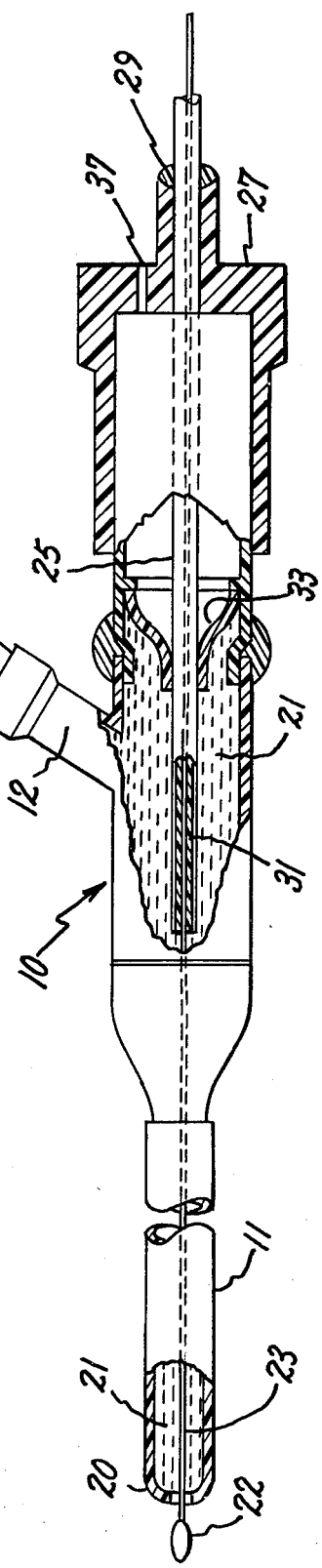
FIG. 2 is a view like that of FIG. 1 showing the sensing electrode in the "calibration" position.
Figure 2:
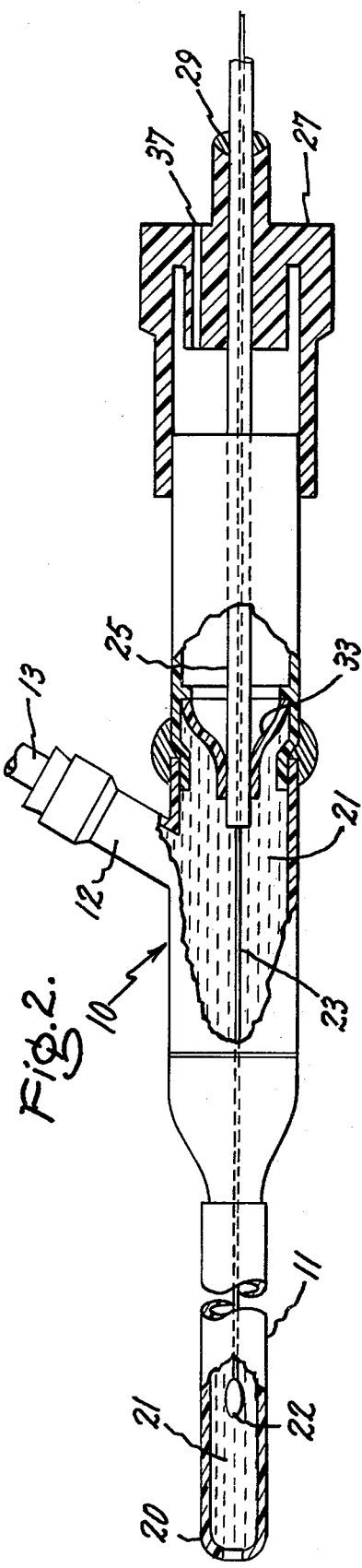

Pressure-equalizing opening 37 in cap 29 facilitates movement of the cap without effecting the gland pressure seal to position tube 25 and electrode tip 22, as illustrated in FIGS. 1 and 2.

In the preferred practice of this invention, guard tube 25 is of metal such as that of a catheter needle and, as illustrated, it is rigidly bonded to both cap 29 and electrode 23 to enable precise adjustment of the position of electrochemically active portion 22 relative to leading end 20 of the catheter. Further, cap 27 is sized to fit over the trailing end of the catheter and locked by means of a Luer fitting for easy manual adjustment. The guard tube function is necessary for the protection of the sensing electrode insulation against abrasion by tube 33, and also to insure liquid-tight sealing by tube 33 which in commercially available catheters is not designed to sealingly fit the sensing electrode lead. In addition, guard tube 25 transmits axially-applied forces from cap 27 to the insulated lead of sensing electrode 23.

It will be understood that the sensor assembly of this invention is applicable to the monitoring or measurement of pH, potassium, calcium and other ions in the blood and also is not limited to use only in arterial applications. In other words, the basic new principles of design and operation of the sensors of this invention apply generally to specific in vivo sensing systems and devices incorporating the sensing electrode and reference electrode combination together with a capability of coupling and uncoupling the electrodes for the alternative purposes of measurement and calibration. As a practical matter, however, this invention is not applicable to non-injectable calibrating solutions.

The following experiment further illustrates the practice of this invention:

EXAMPLE

The in vivo blood sensor assembly of FIGS. 1 and 2 was provided with a pH sensing electrode 23 in the form of a polymer membrane pH sensor as described and claimed in U.S. Pat. No. 3,743,588, assigned to the assignee hereof. The insulated lead of electrode 23 extended through guard tube 25 positioned as shown in FIG. 2 with its leading end within catheter 11 adjacent to side arm 12 so that electrochemically active tip 22 was about 1.5 centimeter within the open leading end 20 of the catheter. With these and the related components assembled and secured together, as above described, a buffered flush solution (25 mM $Na_2PO_4$, 25 mM $KHPO_4$ and 80 mM NaCl having a pH of 6.735 ± 0.005 at 25° C) was supplied under pressure through drip line 15 and side arm 12 as described in U.S. patent application Ser. No. 620,707. Reference electrode 17 was a chlorided silver wire sealed into one end of a small diameter plastic tube filled with a solution of 4N potassium chloride gelled with 2 weight percent Agar-Agar. The potassium chloride electrolyte furnished the chloride ion concentration to establish the electrochemical potential of the silver/silver chloride couple, and it also served as an intermediate electrolyte bridge between the chlorided silver wire and the flush solution with which it was in contact at the opposite end of the plastic tube. The electrodes were connected to a pH meter (Instrumentation Laboratories Model 245) by means of cables shielded so that pick-up noise was reduced to less than 1 millivolt. The sensor assembly was rinsed by passing about 1 milliliter of flush solution through the catheter and then the pH meter adjusted to read 6.735 and sensing electrode 22 was moved to the measurement position of FIG. 1. Six external solutions, each of different pH at 25° C, were tested at that temperature by this sensor assembly and by a glass electrode with the following results:

TABLE

| External Solution No. | Sensor/Catheter Calibrate | Sensor/Catheter Measure | Glass Electrode |
|---|---|---|---|
| 1 | (6.735) | 6.738 | 6.735 |
| 2 | (6.735) | 7.312 | 7.315 |
| 3 | (6.735) | 7.532 | 7.539 |
| 4 | (6.735) | 7.167 | 7.192 |
| 5 | (6.735) | 7.332 | 7.323 |
| 6 | (6.735) | 7.469 | 7.468 |

The utility of this new sensor assembly for its intended purpose is established by these results.

Modifications contemplated in the illustrated device of this invention include thermostating of the reference electrode so that variations in temperature will not affect its potential. This would be desirable if a very high degree of pH measurement accuracy is required.

What I claim as new and desire to secure by Letters Patent of the United States is:

1. A specific ion sensor for in vivo use which can be calibrated in situ without withdrawing blood from a patient which comprises
   a. an elongated insulated sensing electrode having an electrochemically active portion at one end exposed for contact with blood in a patient's blood vessel and having its other end exposed for connection to recording equipment,
   b. a guard tube receiving and enclosing a portion of the length of the sensing electrode removed from the electrochemically active portion thereof,
   c. a catheter receiving and enclosing a portion of the length of the tube and the sensing electrode and having an open leading end and additionally having a side port and having a trailing end through which the said other end of the sensing electrode extends,
   d. sensing electrode positioning means connected to the sensing electrode at a point removed from the electrochemically active portion for moving the electrode axially relative to the catheter to position the said active portion within the open end of the catheter for calibration purposes and to position said active portion outside the open end of the catheter for in vivo measurement purposes,
   e. drip line means communicating with the catheter through the side port for delivering electrolyte into the catheter at pressure greater than that of a patient's blood at the open end of the catheter,
   f. a reference electrode positioned partially in the drip line means for functional contact with electrolyte flowing to the catheter and having a portion disposed outside the drip line means for connection to recording equipment, g. flexible sealing means secured to the catheter between the side port and the trailing end of the catheter and pressure sealing against an annular portion of the tube to prevent electrolyte flow and blood reflux in the direction of the trailing end of the catheter beyond a predetermined point, and h. sealing means within the guard tube and in contact with an annular portion of the sensing electrode therein to prevent flow of electrolyte through the guard tube.

2. The sensor as set forth in claim 1 in which the guard tube is of metal and the positioning means is a cap attached to the guard tube and adapted to close the trailing end of the catheter.

3. The sensor of claim 1 in which the guard tube is of inside diameter substantially greater than the outside diameter of the insulated portion of the sensing electrode and of outside diameter substantially less than the inside diameter of the catheter.

4. The sensor of claim 1 in which the flexible sealing means is a gland and the sealing means within the guard tube is provided in the form of a plug of inert bonding material positioned to prevent entry of electrolyte into the tube.

* * * * *